United States Patent
Smith et al.

(10) Patent No.: US 9,144,429 B2
(45) Date of Patent: *Sep. 29, 2015

(54) DYNAMIC ORTHOSCOPIC SENSING

(71) Applicant: Smith & Nephew, Inc., Memphis, TN (US)

(72) Inventors: Todd Edward Smith, Hopedale, MA (US); Paul Robert Duhamel, Groton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/224,466

(22) Filed: Mar. 25, 2014

(65) Prior Publication Data

US 2014/0207140 A1      Jul. 24, 2014

Related U.S. Application Data

(63) Continuation of application No. 13/242,336, filed on Sep. 23, 2011, now Pat. No. 8,753,344.

(51) Int. Cl.
*A61B 17/00* (2006.01)
*A61B 17/16* (2006.01)
*A61B 17/32* (2006.01)
*A61B 19/00* (2006.01)

(52) U.S. Cl.
CPC .............. *A61B 17/1626* (2013.01); *A61B 17/16* (2013.01); *A61B 17/32002* (2013.01); *A61B 2017/00075* (2013.01); *A61B 2017/00221* (2013.01); *A61B 2019/464* (2013.01); *A61B 2019/466* (2013.01)

(58) Field of Classification Search
CPC .......................... A61B 17/32002; A61B 17/16
USPC ........................................ 606/79–83, 167–183
See application file for complete search history.

*Primary Examiner* — Andrew Yang
(74) *Attorney, Agent, or Firm* — Chapin IP Law, LLC

(57) ABSTRACT

A dynamic sensing method and apparatus employs microelectromechanical systems (MEMS) and nanoelectromechanical (NEMS) surgical sensors for gathering and reporting surgical parameters pertaining to a drive mechanism of a surgical device, such as speed, rotation, torque and other characteristics of the surgical device. The surgical device employs or affixes the surgical sensor on or about a surgical device for detecting electromechanical characteristics during the surgical procedure. The surgical procedure disposes the medical device in the surgical field responsive to the drive mechanism of a shaver or other endoscopic instrument inserted in a surgical field defined by the surgical procedure.

25 Claims, 6 Drawing Sheets

DYNAMIC ORTHOSCOPIC SENSING

RELATED APPLICATIONS

This application is a continuation of application, U.S. Ser. No. 13/242,336, entitled Dynamic Orthoscopic Sensing, filed Sep. 23, 2011, the entire teaching, disclosure and contents of which are incorporated herein by reference by in their entirety.

BACKGROUND

Design and development of electronics has steadily been following a downsizing trend ever since Gordon Moore, cofounder of Intel® corporation, suggested in 1965 that the transistor density (hence computing power) of a given chip area doubles roughly every 24 months, in a somewhat prophetic assertion that has become widely known as "Moore's Law." Medical devices and apparatus are no exception to the trend of electronics miniaturization. Microelectronics are often employed as sensors for providing diagnostic feedback on routine patient status, such as for sensing pulse, oxygen saturation, body temperature, and fetal vitals during childbirth.

During surgical procedures, sensing often extends to drive mechanisms for surgical instruments, such as an orthoscopic shaver or cutter systems. Orthoscopic surgical devices (and other endoscopic devices) perform minimally invasive procedures through apertures (holes) that provide access to a surgical field, in contrast to traditional open surgery that requires an incision along the entire surgical field. Orthoscopic procedures, therefore, often occur in confined spaces inside the abdominal cavity of a patient, using elongated probes of the orthoscopic surgical instruments. These instruments often require precise manipulation to navigate the narrow clearances of the surgical field. Accordingly, orthoscopic surgical devices and instruments avoid bulky and/or unwieldy design which may interfere with precise manipulations of the surgeon.

SUMMARY

A dynamic sensing method and apparatus employs microelectromechanical systems (MEMS) and nanoelectromechanical (NEMS) surgical sensors for gathering and reporting surgical parameters pertaining to a drive mechanism of a surgical device, such as speed, rotation, torque and other characteristics of the surgical device. Micromechanical devices, in contrast to conventional electronics, are small machines adapted for physical transitions such as movement of levers, gears, and transducers, in addition to computational execution the surgical device employs or affixes the surgical sensor on or about a surgical device for detecting electromechanical characteristics during the surgical procedure. The surgical procedure disposes the medical device in the surgical field responsive to the drive mechanism of a shaver or other endoscopic instrument inserted in a surgical field defined by the surgical procedure.

Conventional sensors for providing diagnostic feedback for orthoscopic procedures tend to crowd the surgical field and require additional tethers (wired connections) to the instruments. The reduced size of the surgical sensor allows nonintrusive placement in the surgical field, such that the sensor does not interfere with or adversely affect the drive operation of the surgical device for which it is to measure surgical parameters. The reduced size is also favorable to manufacturing costs and waste for single use and disposable instruments, which are discarded after usage on a single patient.

In configurations disclosed below, a surgical device drive employs MEMS or NEMS surgical sensors to provide performance data and statistics to the drive mechanism for use as feedback and control parameters to vary, for example, shaver speed and rotation proportional to a pump evacuating the surgical field. The surgical sensor is affixed or otherwise disposed on a "truck" or rotating hub of the shaver. A cutting blade extends axially from the truck for transferring rotary motion to a cutting edge at an opposed end of the cutting blade. The truck rotates in response to the drive mechanism for providing a cutting and/or extraction force to the shaver, by rotating in a constant or oscillating manner to transfer cutting force to the cutting edge. The surgical sensor detects rotation, speed, and torque of the shaver, for detecting speed indicative of an incision rate, and torque which may indicate an upper limit of structural stability of the truck and blade assembly.

Configurations herein are based, in part, on the observation that conventional approaches employ RFID (Radio Frequency Identification) tags on surgical tools and equipment for tracking during a surgical procedure. While RFIDs can be fabricated to be small and passive (i.e. externally powered by the triggering signal), computation and execution power is limited. Unfortunately, therefore, conventional approaches to parameter sensing suffer from the shortcoming that response is typically limited to identification of the device or instrument on which the RFID is affixed, and information other than identity is unavailable, due to limited computational ability that may be encoded on an RFID.

Accordingly, configurations herein substantially overcome the above described shortcomings by providing an unobtrusive sensor disposed on a surgical device responsive to a drive mechanism for sensing dynamic attributes such as speed, rotation and torque and for transmitting the sensed attributes via a wireless interface to a drive source for responsive control. The wireless interface allows affixation of the surgical sensor to a rotating or moving component of the surgical device, and the micromechanical nature allows placement in a noninterfering location that does not adversely affect surgical device operation.

In further detail, the method provides dynamic surgical feedback during a surgical or therapeutic procedure by identifying a sensory area on a surgical device, such that the sensory area is adapted to receive an integrated micromechanical device and responsive to sensed electromechanical stimuli during a surgical procedure. The surgical device is coupled to a drive source for performing surgical manipulations, and the integrated micromechanical device is affixed to the sensory area for detecting surgical parameters dynamically during the surgical procedure. The integrated micromechanical device (micromechanical device) maintains wireless communication with a controller responsive to the integrated micromechanical device for dynamically receiving the detected surgical parameters from the integrated micromechanical device during the surgical procedure, and placement in a non-interfering sensory area provides that the sensed surgical parameters are unaffected by the presence of the micromechanical device due to unobtrusive placement of the integrated micromechanical device at the sensory area.

In a particular configuration, the claimed approach has particular utility in an endoscopic procedure such as a knee joint surgery, discussed herein as an example application. In a medical device environment, the method controls a surgical extraction device, such as a shaver, and including an integrated micromechanical device configured for rotational sensing, and establishes a wireless connection from the micromechanical device to a controller for sending sensed rotational parameters. An attachment mechanism affixes the integrated micromechanical device to a rotary hub for driving a surgical blade, in which the rotary hub is responsive to a drive source for rotating the surgical blade for cutting and extraction of surgical matter. As the rotary hub restricts physical connections due to movement (rotation), the wireless connection mitigates the need for physical tethered connections. The surgeon disposes the surgical blade in a surgical field for performing therapeutic manipulations from rotation of the surgical blade, and the micromechanical device senses, based on the rotation of the hub, the rotational parameters caused by centrifugal forces exerted on the micromechanical device. The micromechanical device sends the sensed rotational parameters to a controller for deriving surgical parameters, in which the controller is coupled to a pump and configured to control the pump in response to the derived surgical parameters, therefore providing proportional control for the pump in response to shaver activity.

Alternate configurations of the invention include a multi-programming or multiprocessing computerized device such as a multiprocessor, controller or dedicated computing device or the like configured with software and/or circuitry (e.g., a processor as summarized above) to process any or all of the method operations disclosed herein as embodiments of the invention. Still other embodiments of the invention include software programs such as a Java Virtual Machine and/or an operating system that can operate alone or in conjunction with each other with a multiprocessing computerized device to perform the method embodiment steps and operations summarized above and disclosed in detail below. One such embodiment comprises a computer program product that has a non-transitory computer-readable storage medium including computer program logic encoded as instructions thereon that, when performed in a multiprocessing computerized device having a coupling of a memory and a processor, programs the processor to perform the operations disclosed herein as embodiments of the invention to carry out data access requests. Such arrangements of the invention are typically provided as software, code and/or other data (e.g., data structures) arranged or encoded on a computer readable medium such as an optical medium (e.g., CD-ROM), floppy or hard disk or other medium such as firmware or microcode in one or more ROM, RAM or PROM chips, field programmable gate arrays (FPGAs) or as an Application Specific Integrated Circuit (ASIC). The software or firmware or other such configurations can be installed onto the computerized device (e.g., during operating system execution or during environment installation) to cause the computerized device to perform the techniques explained herein as embodiments of the invention.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example configuration of a medical device environment employing dynamic feedback via micromechanical surgical sensors. In the example shown, the surgical device is a surgical shaver responsive to a drive source for providing rotational movement for excising and removing surgical material such as bone and tissue from the surgical field. The surgical sensor is affixed to a so-called truck, or rotating hub, responsive to the drive source. A cutting edge at the end of the cutting blade rotates or oscillates to extract the surgical material, and a hollow interior of the tubular blade allows evacuation by a pump, also controlled by the drive source.

Figure 1:
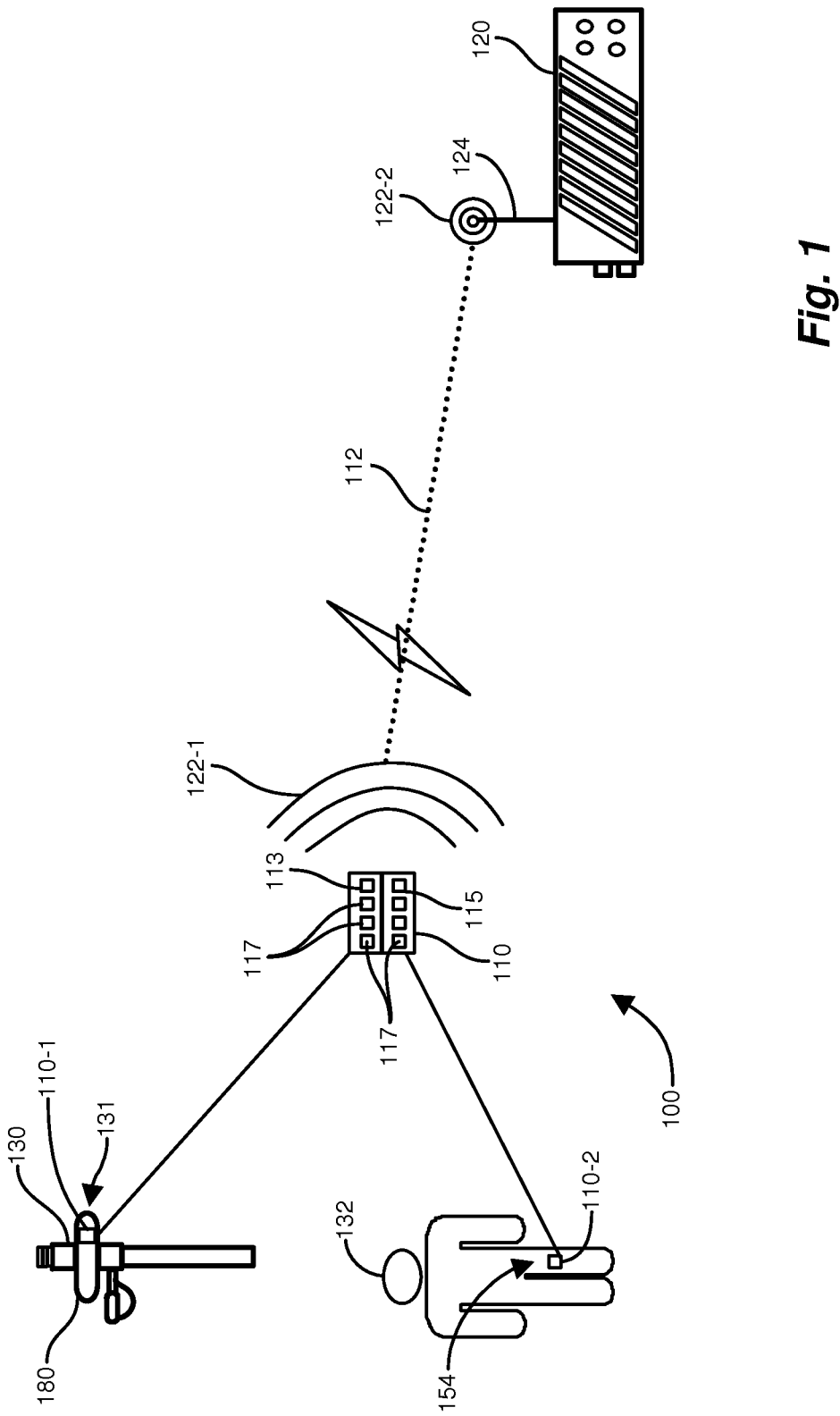
FIG. 1 is a context diagram of a medical device environment suitable for use with configurations disclosed herein.

FIG. 1 is a context diagram of a medical device environment 100 suitable for use with configurations disclosed herein. Referring to FIG. 1, the medical device environment 100 employs an integrated micromechanical device (micromechanical device) 110 for placement within the surgical environment, such as in a shaver 130, shown as 110-1 or at a surgical field 154 of the patient 132, shown as 110-2 (110 generally). The micromechanical device 110, in a particular configuration, is a MEMS or NEMS device and maintains a wireless connection 112 to a drive controller 120 or other centralized controller responsive to signals 122 to (122-1) and from (122-2) a wireless antenna 124. The micromechanical device 110 includes a receiver 115 responsive to the signals 122-2 from the antenna 124 for requesting sensing of surgical parameters, and a transmitter 113 configured to transmit the sensed surgical parameters back to the controller 120 via signals 122-1, and may include other sensing, computation, and power components 117. The micromechanical device 110 may be passive, such that the signals 122-2 also provide power to the device 110, and is sufficiently small such that received signals 122-2 permit operation and transmission of sensed parameters 122-1, and the micromechanical device 110 may have other sensory areas, processing functions or mechanical features responsive to the signal 122-2.

Placement of the micromechanical device 110 is such that it directly senses surgical parameters such as speed, rotation and torque, and may include affixation to the interior of a surgical shaver 130, shown as micromechanical device 110-1, or may operate directly within the surgical site 154. The micromechanical device 110, once disposed, activates from a signal 122-2 from the controller 120, and performs sensing, computation and transmission tasks for returning the sensed surgical parameters 122-1. The shaver 130 configuration affixes the micromechanical device 110-1 to the truck or hub 180 which is then inserted into a surgical site for surgical cutting and evacuation, discussed further below with respect to FIG. 3.

Figure 2:
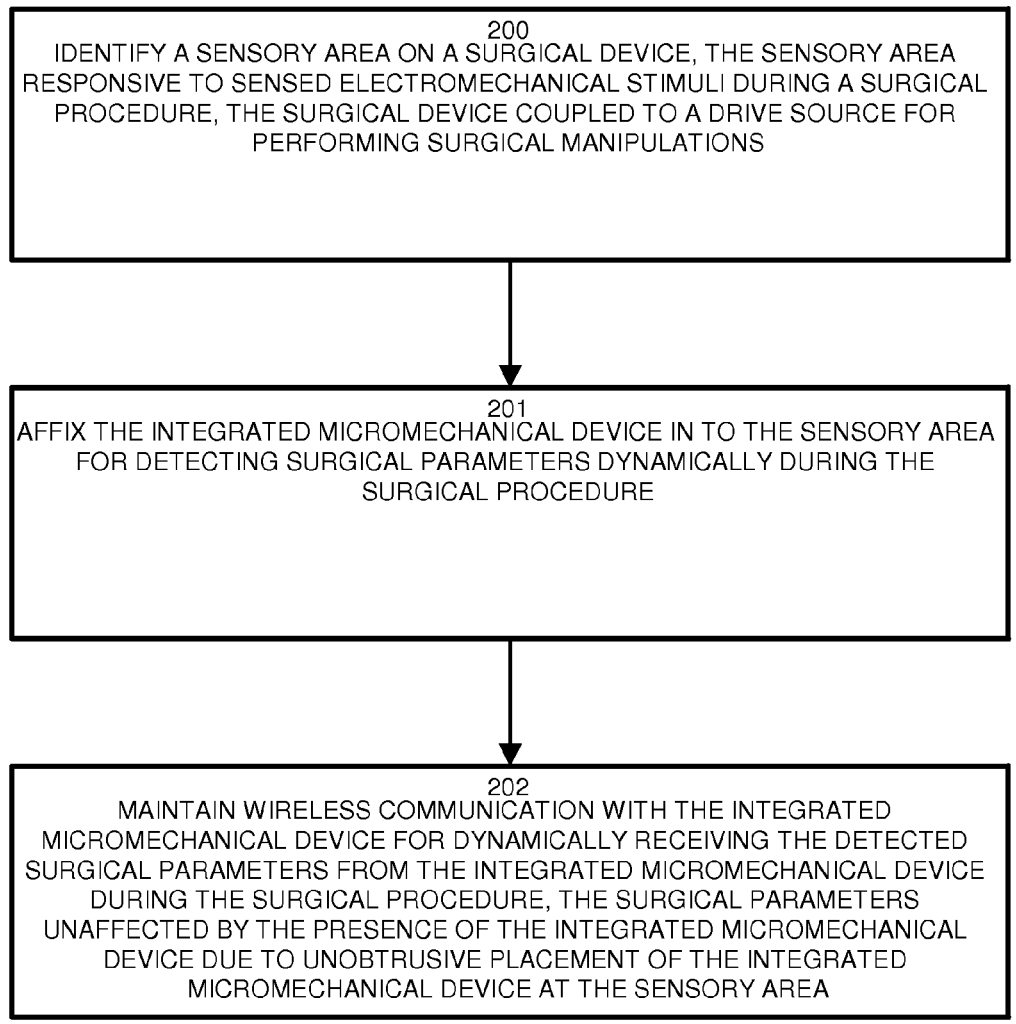
FIG. 2 is a flowchart of dynamic parameter sensing as disclosed herein.

FIG. 2 is a flowchart of dynamic parameter sensing as disclosed herein. In the surgical device environment 100, the disclosed method of controlling a surgical appliance includes, at step 200, identifying a sensory area on a surgical device 130, such that the sensory area 131 is responsive to sensed electromechanical stimuli during a surgical procedure. The surgical device 130 couples to a drive source 120 for performing surgical manipulations such as drilling or pumping. In a rotary device such as the example shaver 130, for example, the sensory area 131 may be on a rotating part subject to centrifugal forces from the drive source 120 during operation.

Various sensing capabilities may be employed in the micromechanical device 110-1, such as variable resistance, pressure sensing, gyroscopic and strain gauge sensing, to name several.

An attachment mechanism affixes the integrated micromechanical device 110-1 to the sensory area 131 for detecting surgical parameters dynamically during the surgical procedure, as shown at step 201. The attachment mechanism may be any suitable affixation, such as pins, glue, solvent welding, or may be a feature of the surgical instrument fabrication, such as a cavity or pocket formed during casting, for example.

The micromechanical device 110 maintains wireless communication with the drive controller 120 for dynamically receiving the detected surgical parameters as signals 122-1 from the integrated micromechanical device 110 during the surgical procedure, as depicted at step 202. Location and size of the device 110 is such that the surgical parameters are unaffected by the presence of the integrated micromechanical device due to unobtrusive placement of the integrated micromechanical device at the sensory area 131.

Figure 3:
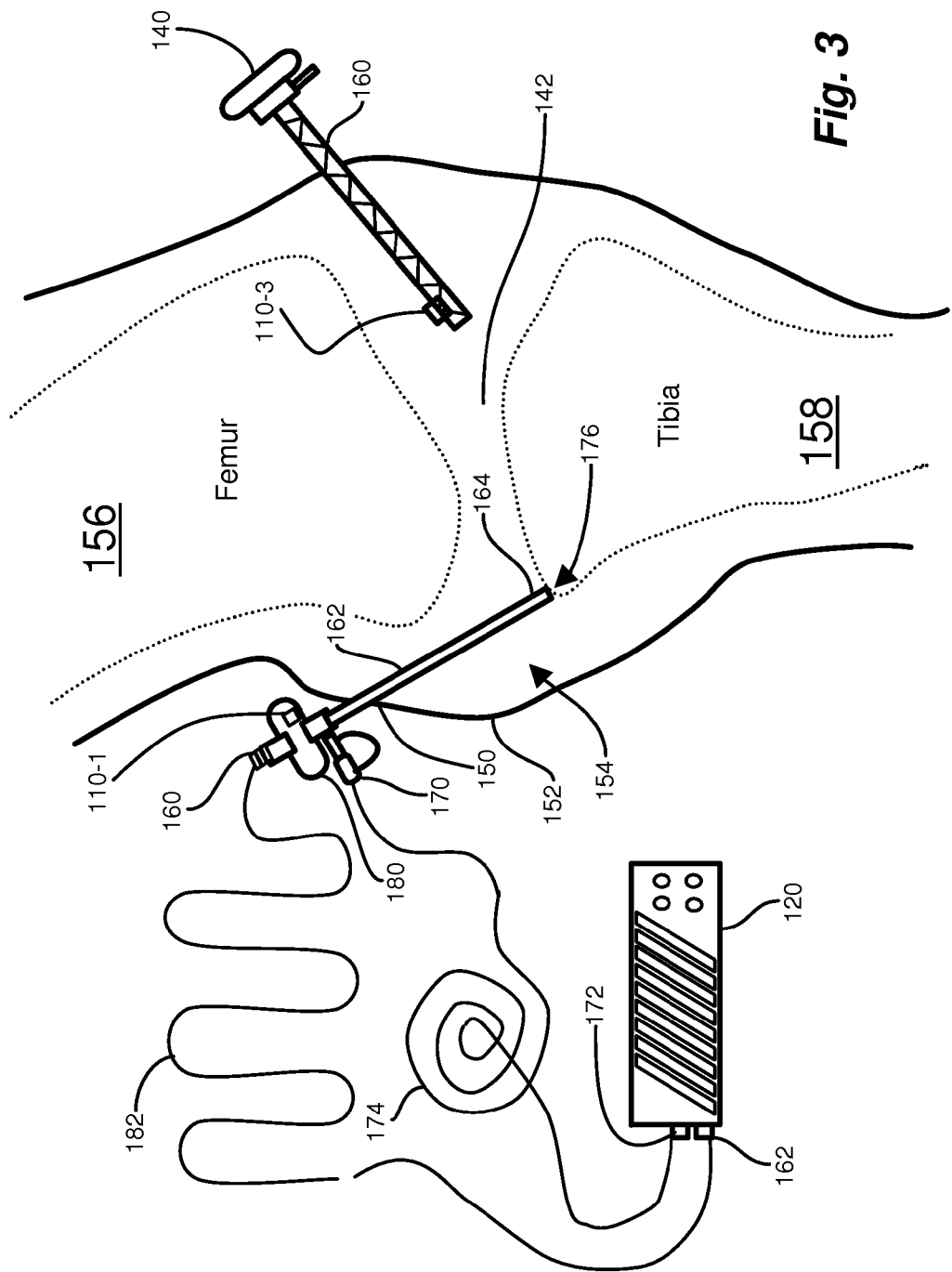
FIG. 3 is a diagram of sensor deployment in the environment of FIG. 1.
Figure 4:
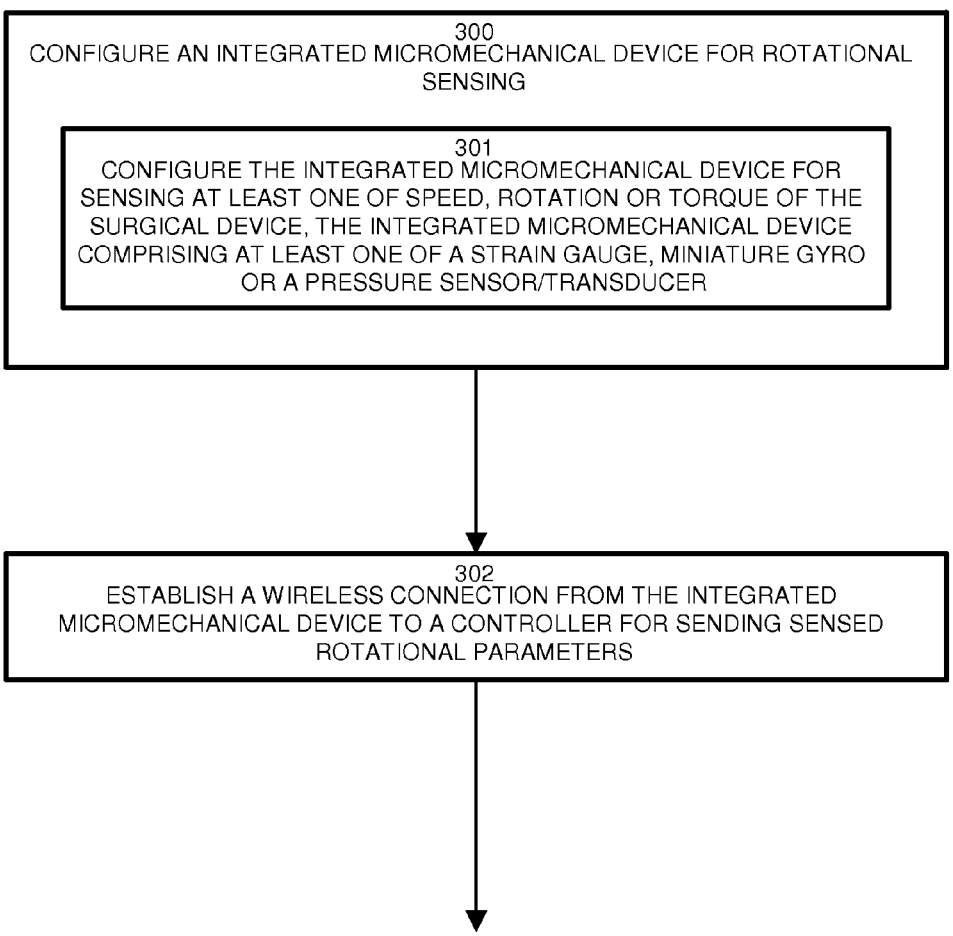
FIGS. 4-6 are a flowchart of endoscopic sensory arrangements during a surgical procedure.
Figure 5:
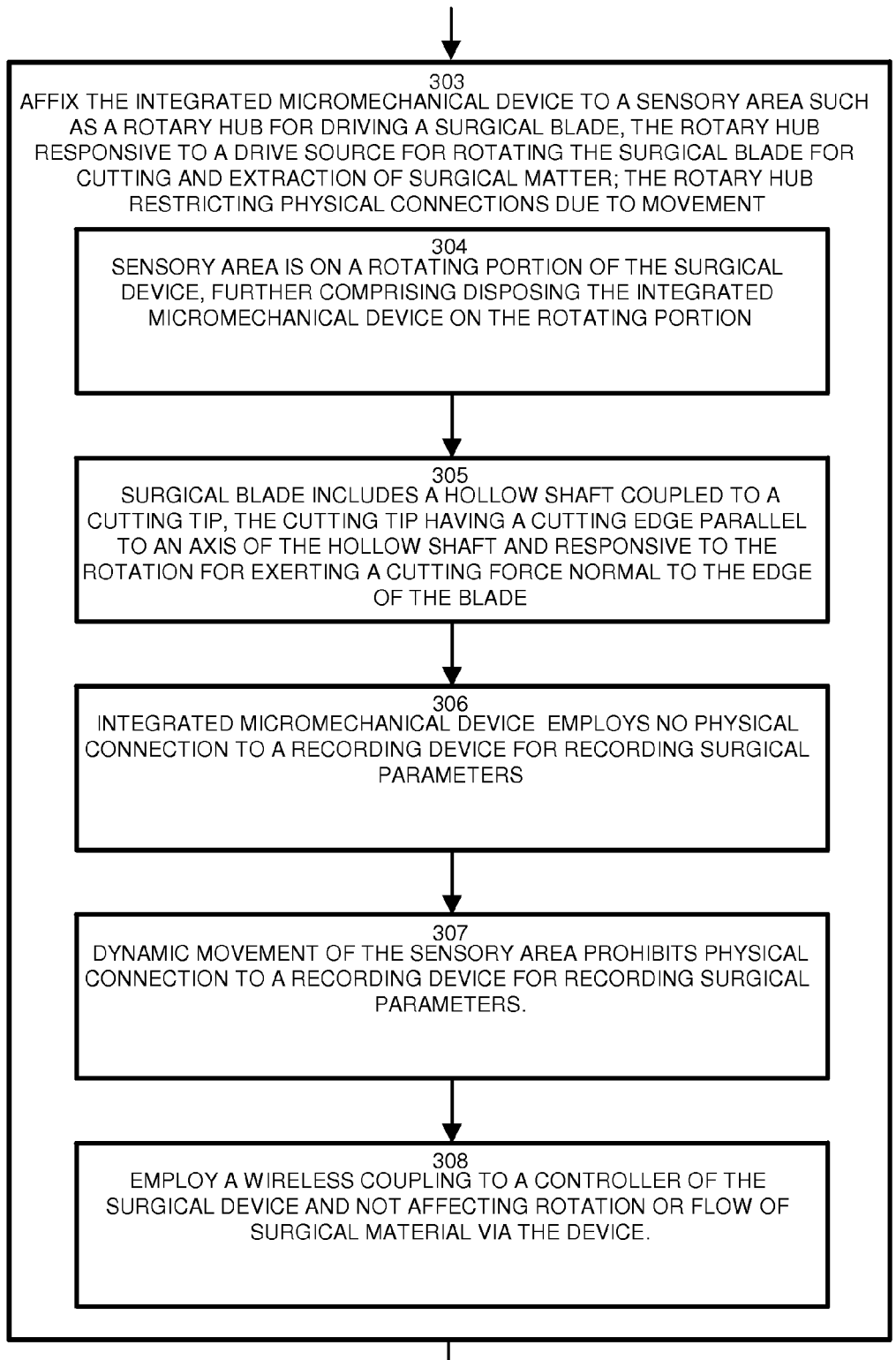
Figure 6:
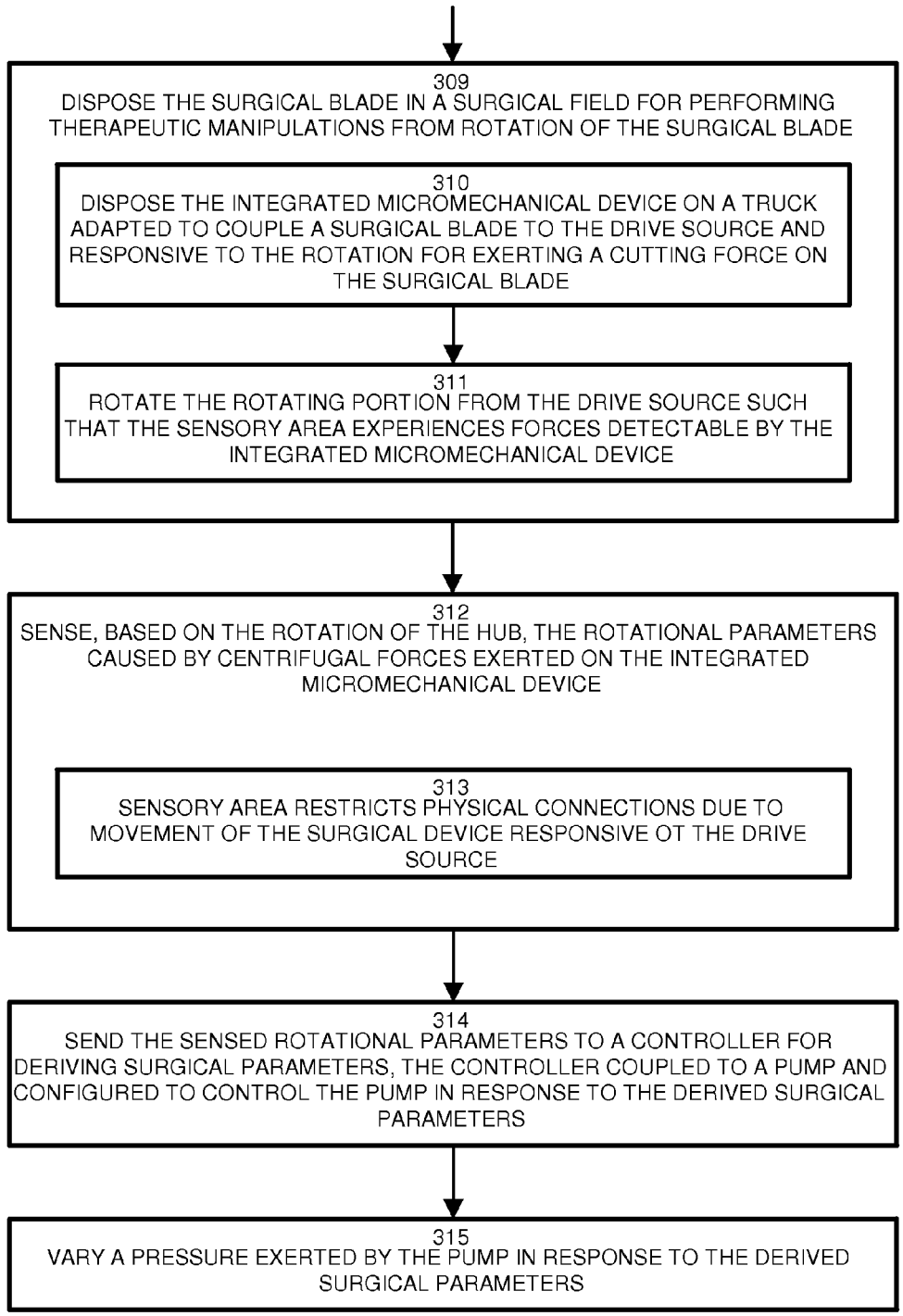

FIG. 3 is a diagram of sensor deployment in the environment of FIG. 1. Referring to FIGS. 1 and 3, an example arrangement of micromechanical device 110 deployment in an endoscopic knee procedure is depicted. A surgeon disposes the shaver 130 through an endoscopic aperture 150 in the knee 152 of a patient. The shaver 130 extends through skin and soft tissue into a surgical void 154 between the femur 156 and tibia 158. The shaver 130 includes a drive connection 160, for coupling to a drive port 162 of the controller 120 via a drive cable 182. The drive connection 160 may receive electric, pneumatic, hydraulic, or other suitable drive medium for powering the hub 180 and attached surgical blade 162 and cutting edge 164. The shaver 130 also includes a suction port 170 for coupling to an evacuation port 172 via a tube set 174. The drive controller 120 applies suction (typically via a surgical pump) for evacuating surgical material from the shaver via the hollow core 176 of the surgical blade 162. Alternatively, a separate pump may be employed distinct from the drive controller 120 powering the shaver 130. The procedure may also include one or more cannulas 140 having a micromechanical device 110-3 affixed to the interior of a delivery tube 160 of the cannula 140 for sensing pressure, flow and temperature of saline pumped through the cannula delivery tube 160, and for additional irrigation or evacuation (suction) of the surgical site FIGS. 4-6 are a flowchart of endoscopic sensory arrangements during a surgical procedure. Referring to FIGS. 1 and 3-6, a method of controlling a surgical extraction device such as a shaver 130 includes configuring an integrated micromechanical device 110-1 for rotational sensing, as depicted at step 300. In the example arrangement, this includes configuring the micromechanical device 110-1 for sensing at least one of speed, rotation or torque of the surgical device, in which the integrated micromechanical device comprises at least one of a strain gauge, miniature gyro or a pressure sensor/transducer, as disclosed at step 301. Various sensing and computational capabilities may be configured or fabricated on the micromechanical device 110. In particular, rotational sensing due to centrifugal force, or detecting alternating orientations through a gravitational field, may indicate rotation. The micromechanical device 110 is also is equipped for establishing a wireless connection 122-1 from the integrated micromechanical device 110-1 to a controller 120 for sending sensed rotational parameters, as depicted at step 302.

The MEMS equipped shaver 130 affixes the integrated micromechanical device 110 to a sensory area 131 such as a rotary hub 180 for driving a surgical blade, as disclosed at step 303, in which the rotary hub 180 is responsive to a drive source or controller 120 for rotating the surgical blade 162 for cutting and extraction of surgical matter. The wireless capability provides for gathering of surgical parameters despite the rotary hub 180 restricting physical connections due to movement (rotation). In the shaver 130 example shown, the sensory area 131 is on a rotating portion of the surgical device (hub of shaver 130), and affixation disposes the integrated micromechanical device 110 on the rotating portion 180, as depicted at step 304.

The surgical blade 162 extending from the hub 180 includes a hollow shaft or bore 176 coupled to a cutting tip 164, such that the cutting tip 164 has a cutting edge parallel to an axis of the hollow shaft and responsive to the rotation for exerting a cutting force normal to the edge of the blade 162, as disclosed at step 305. The micromechanical device 110 therefore employs no physical connection to a recording device for recording the surgical parameters due to the rotation of the hub 180, as shown at step 306, as dynamic movement of the sensory area 131 prohibits physical connection to a recording device for recording surgical parameters, as depicted at step 307. Rather, gathering surgical parameters is facilitated from unobtrusive placing of a wireless coupling (i.e. transmitter 113) to a controller of the surgical device 130 that does not affecting rotation or flow of surgical material via the device 130, as disclosed at step 308.

In the course of a surgical or therapeutic procedure, a surgeon disposes the surgical blade 162 into the surgical field 154 for performing therapeutic manipulations from rotation of the surgical blade 162, as shown at step 309. This includes disposing the micromechanical device 110 on a truck 180 adapted to couple the surgical blade 162 to the drive source 120 and responsive to the rotation for exerting a cutting force on the cutting edge 164 via the surgical blade 162 via, as depicted at step 310. The drive source 120 rotates the rotating portion 180 via a drive cable 182 from the drive controller 120 such that the sensory area 131 experiences forces detectable by the micromechanical device 110-1, as disclosed at step 311.

The micromechanical device 110 senses, based on the rotation of the hub 180, the rotational parameters caused by centrifugal forces exerted on the micromechanical device 110-1, as shown at step 312. The sensory area 131 restricts physical connections due to movement of the surgical device 130 responsive to the drive source 120, as depicted at step 313, such as rotation of the hub 180 or other drive mechanism. Alternate configurations may deploy various sensing capabilities on the micromechanical device 110. A strain gauge may be employed to detect torque by sensing surface variations on the hub 180 for sensing excessive and damaging force that could fracture the hub 180. Centrifugal or gravitational variations may be sensed by a pressure sensitive resistor or gyroscope, for example. In the particular shaver arrangement shown, the micromechanical device 110-1 sends the sensed rotational or other sensed parameters to the controller 120 for deriving the surgical parameters, in which the controller 120 is coupled to a pump and configured to control the pump in response to the derived surgical parameters, as depicted at step 314. In such a configuration, the drive controller 120 varies pressure exerted by the pump in response to the derived surgical parameters, as disclosed at step 315, to provide a level of suction pressure proportional to the evacuation of surgical material resulting from the speed and cutting force of the surgical blade 162. prevailing Conventional approaches are shown by U.S. Publication No. 2007/0078484, to Talarico et al. (Talarico '484), which discloses a surgical grasper comprising a handle and two jaws operably connected to and actuated by the handle. A sensor is located on an inner surface of one or both of the jaws for direct measurement of an amount of pressure or force being applied with the grasper, referring to paragraph [0006]. While Talarico '484 suggests MEMS based sensors at paragraph [0047]-[0048], the sensors are for detecting pressure or force between the jaws. In contrast to the proposed approach, there is no showing, teaching, or disclosure of rotary based parameters such as torque, speed or rotation. Further, such rotary parameters would be inapplicable to the linear forces pertaining to the closure of the jaw surfaces.

Another application, U.S. Publication No. 2008/0167672 by Giordano (Giordano '672), teaches a surgical instrument comprising at least one sensor transponder, such as endoscopic or laparoscopic surgical instruments. Giordano '672 is directed to surgical instruments where some feature of the instrument, such as a free rotating joint, prevents or otherwise inhibits the use of a wired connection to the sensor(s), as discussed at [0033]. While Giordano '672 refers to MEMS technology, the '672 publication only employs sensors in the articulated jaws of the end effector 12, as disclosed at paragraph [0057], and makes no suggestion of continued rotation as in a shaft drive. Accordingly, Giordano '672 does not show, teach or disclose MEMS sensors disposed in a rotary configuration or coupling for sensing and transmitting operational parameters related to the rotating movement, in contrast to the proposed approach.

U.S. Publication No. 2005/0131390 ('390) teaches a surgical stapler with an end effector including a staple cartridge assembly, and an anvil operatively associated with the staple cartridge, such that the staple cartridge and the anvil are movably connected to one another to bring one into juxtaposition relative to the other. Each of the staple cartridge and the anvil define tissue contacting surfaces and the MEMS device is operatively connected to the tissue contacting surface of the staple cartridge and the tissue contacting surface of the anvil. A plurality of MEMS devices are connected to the surgical instrument, and the MEMS devices are configured and adapted to measure distance between the tissue contacting surface of the staple cartridge assembly and the tissue contacting surface of the anvil, as discussed at paragraph [0014].

The disclosed MEMS devices in the '390 application are configured and adapted to measure at least one of the amount of pressure applied to tissue and the thickness of tissue clamped between the tissue contacting surface of the staple cartridge assembly and the tissue contacting surface of the anvil, discussed at [0015]. In contrast to the proposed approach, however, there does not appear to be any disclosure of sensors applied to rotary or rotational movement, nor of associated feedback of operational data or parameters relating to rotary motion.

Those skilled in the art should readily appreciate that the programs and methods for measuring surgical parameters as defined herein are deliverable to a user processing and rendering device in many forms, including but not limited to a) information permanently stored on non-writeable storage media such as ROM devices, b) information alterably stored on writeable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and method of measuring surgical parameters has been particularly shown and described with references to embodiments thereof, it will be understood by those skilled in the art that various changes in form and details may be made therein without departing from the scope of the invention encompassed by the appended claims.

What is claimed is:

1. A method of controlling a surgical extraction device comprising:
    affixing an integrated micromechanical device to a rotary hub for driving a surgical blade, the rotary hub responsive to a drive source for rotating the surgical blade for cutting and extraction of surgical matter; the rotary hub restricting physical connections due to movement;
    disposing the surgical blade in a surgical field for performing therapeutic manipulations from rotation of the surgical blade;
    sensing, based on the rotation of the hub, the rotational parameters caused by centrifugal forces exerted on the integrated micromechanical device.

2. The method of claim 1, further comprising:
    establishing a wireless connection from the integrated micromechanical device to a controller for sending sensed rotational parameters
    sending the sensed rotational parameters to a controller for deriving surgical parameters, the controller coupled to a pump and configured to control the pump in response to the derived surgical parameters.

3. The method of claim 1 further comprising varying a pressure exerted by a pump in response to the derived surgical parameters.

4. In a surgical device environment, a method of controlling a surgical appliance comprising:
    identifying a sensory area on a surgical device, the sensory area adapted to receive an integrated micromechanical device and responsive to sensed electromechanical stimuli during a surgical procedure, the surgical device coupled to a drive source for performing surgical manipulations and adapted for insertion into an endoscopic site; and
    affixing the integrated micromechanical device to the sensory area for detecting surgical parameters dynamically during the surgical procedure.

5. The method of claim 4 further comprising:
    maintaining wireless communication with a controller, the controller responsive to the integrated micromechanical device for dynamically receiving the detected surgical parameters from the integrated micromechanical device during the surgical procedure, the surgical parameters unaffected by the presence of the integrated micromechanical device due to unobtrusive placement of the integrated micromechanical device at the sensory area.

6. The method of claim 4 wherein the sensory area is on a rotating portion of the surgical device, further comprising disposing the integrated micromechanical device on the rotating portion; and
    rotating the rotating portion from the drive source such that the sensory area experiences forces detectable by the integrated micromechanical device.

7. The method of claim 6 wherein disposing further comprises disposing the integrated micromechanical device on a truck adapted to couple a surgical blade to the drive source and responsive to the rotation for exerting a cutting force on the surgical blade.

8. The method of claim 7 wherein the surgical blade includes a hollow shaft coupled to a cutting tip, the cutting tip having a cutting edge parallel to an axis of the hollow shaft and responsive to the rotation for exerting a cutting force normal to the edge of the blade.

9. The method of claim 4 wherein the integrated micromechanical device employs no physical connection to a recording device for recording surgical parameters.

10. The method of claim 9 wherein dynamic movement of the sensory area prohibits physical connection to a recording device for recording surgical parameters.

11. The method of claim 10 wherein affixing includes unobtrusive placement employing a wireless coupling to a controller of the surgical device and not affecting rotation or flow of surgical material via the device.

12. The method of claim 4 wherein the sensory area restricts physical connections due to movement of the surgical device responsive to the drive source.

13. The method of claim 12 further comprising configuring the integrated micromechanical device for sensing at least one of speed, rotation or torque of the surgical device, the integrated micromechanical device comprising at least one of a strain gauge, miniature gyro or a pressure sensor/transducer.

14. A surgical appliance comprising:
a sensory area on a surgical device, the sensory area adapted to receive an integrated micromechanical device and responsive to sensed electromechanical stimuli during a surgical procedure, the surgical device coupled to a drive source for performing surgical manipulations;
an attachment mechanism for affixing the integrated micromechanical device to the sensory area for detecting surgical parameters dynamically during the surgical procedure,
wherein the sensory area is on a rotating portion of the surgical device responsive to rotation from a drive source for rotating the rotating portion from the drive source such that the sensory area experiences forces detectable by the integrated micromechanical device.

15. The device of claim 14, further comprising:
a wireless transmitter for maintaining wireless communication with a controller for dynamically receiving the detected surgical parameters from the integrated micromechanical device during the surgical procedure, the surgical parameters unaffected by the presence of the integrated micromechanical device due to unobtrusive placement of the integrated micromechanical device at the sensory area.

16. The surgical appliance of claim 14 wherein the integrated micromechanical device is disposed on a truck adapted to couple a surgical blade to the drive source and responsive to the rotation for exerting a cutting force on the surgical blade.

17. The surgical appliance of claim 16 wherein the surgical blade includes a hollow shaft coupled to a cutting tip, the cutting tip having a cutting edge parallel to an axis of the hollow shaft and responsive to the rotation for exerting a cutting force normal to the edge of the blade.

18. The surgical appliance of claim 14 wherein the integrated micromechanical device is devoid of a physical connection to a recording device for recording surgical parameters.

19. The surgical appliance of claim 18 wherein dynamic movement of the sensory area prohibits physical connection to a recording device for recording surgical parameters.

20. The surgical appliance of claim 19 wherein affixing includes unobtrusive placement employing a wireless coupling to a controller of the surgical device and not affecting rotation or flow of surgical material via the device, the sensory area restricting physical connections due to movement of the surgical device responsive to the drive source.

21. The surgical appliance of claim 20 wherein the integrated micromechanical device includes structures for sensing at least one of speed, rotation or torque of the surgical device.

22. The integrated micromechanical device of claim 20 further comprising at least one of a strain gauge, miniature gyro or a pressure sensor/transducer.

23. In a surgical device environment, a method of controlling a surgical appliance comprising:
identifying a sensory area on a surgical device, the sensory area responsive to sensed electromechanical stimuli during a surgical procedure, the surgical device coupled to a drive source for performing surgical manipulations;
affixing the integrated micromechanical device to the sensory area between the drive source and a surgical site;
detecting centrifugal forces applied to the sensory area of the surgical device.

24. The surgical device of claim 23 further comprising:
maintaining wireless communication with a controller, the controller responsive to the integrated micromechanical device for dynamically receiving at least one detected surgical parameter from the integrated micromechanical device during the surgical procedure.

25. The method of claim 23 further comprising detecting alternating gravitational forces indicative of rotary movement applied to the sensory area of the surgical device.

* * * * *